United States Patent
Letang et al.

(10) Patent No.: US 10,894,146 B2
(45) Date of Patent: Jan. 19, 2021

(54) INTRODUCTION OF A CATHETER IN A VEIN

(71) Applicant: Vygon, Ecouen (FR)

(72) Inventors: Fabien Letang, Morienval (FR); Francois Rochiccioli, Parmain (FR)

(73) Assignee: Vygon

( * ) Notice: Subject to any disclaimer, the term of this patent is extended or adjusted under 35 U.S.C. 154(b) by 345 days.

(21) Appl. No.: 15/722,113

(22) Filed: Oct. 2, 2017

(65) Prior Publication Data
US 2018/0117283 A1    May 3, 2018

(30) Foreign Application Priority Data
Sep. 30, 2016    (FR) ...................................... 16 59447

(51) Int. Cl.
| A61M 25/06 | (2006.01) |
| A61M 25/00 | (2006.01) |
| A61M 39/10 | (2006.01) |
| A61M 25/09 | (2006.01) |

(52) U.S. Cl.
CPC .... *A61M 25/0606* (2013.01); *A61M 25/0097* (2013.01); *A61M 25/065* (2013.01); *A61M 25/0662* (2013.01); *A61M 39/10* (2013.01); *A61M 25/005* (2013.01); *A61M 25/09025* (2013.01)

(58) Field of Classification Search
CPC ........ A61M 25/0606; A61M 25/09016; A61M 25/09025; A61M 25/0097; A61M 25/065
See application file for complete search history.

(56) References Cited

U.S. PATENT DOCUMENTS

| 4,468,224 | A | * | 8/1984 | Enzmann | A61M 25/06 604/168.01 |
| 4,650,472 | A | * | 3/1987 | Bates | A61M 25/09 600/435 |
| 5,019,040 | A | | 5/1991 | Itaoka et al. | |
| 5,304,140 | A | * | 4/1994 | Kugo | A61M 25/0009 604/529 |
| 5,478,331 | A | | 12/1995 | Heflin et al. | |
| 6,156,016 | A | * | 12/2000 | Maginot | A61M 25/0028 604/264 |
| 2003/0187411 | A1 | | 10/2003 | Constantz | |
| 2015/0320977 | A1 | * | 11/2015 | Vitullo | A61M 25/0113 604/510 |

FOREIGN PATENT DOCUMENTS

FR       2996141 A1    4/2014

OTHER PUBLICATIONS

Search Report for Application No. FR1659447 dated Jun. 16, 2017.

* cited by examiner

*Primary Examiner* — Nathan R Price
*Assistant Examiner* — Melissa A Snyder
(74) *Attorney, Agent, or Firm* — Lerner, David, Littenberg, Krumholz & Mentlik, LLP

(57) ABSTRACT

The invention relates to a method for introducing a catheter in a vein, comprising the following steps:
 puncturing the vein,
 introducing a guide in the punctured vein,
 fixing a catheter on the distal coupler of a connector,
 introducing a mandrel in the catheter,
 introducing the set formed by the catheter and the mandrel in the vein by having said set slide on the guide,
 withdrawing the mandrel and the guide, and
 connecting a fluid injection device on the second proximal coupler of the connector.

18 Claims, 6 Drawing Sheets

INTRODUCTION OF A CATHETER IN A VEIN

FIELD OF THE INVENTION

The invention relates to placing a linear guide in a vein and introduction of a catheter in the vein, especially according to the Seldinger technique.

TECHNOLOGICAL BACKGROUND

The Seldinger technique by micropuncture, after having punctured the vein using a needle generally mounted at the end of a syringe, consists in principle of conducting the following steps:

introducing in the vein, via the puncturing needle, a sufficiently flexible guide for following a path having bends, withdrawing the puncturing needle by leaving the flexible guide in place, purging the catheter by means of a physiologic fluid, putting the catheter in place in the vein by threading it on the flexible guide, and withdrawing the flexible guide by leaving the catheter in place.

If needed, when the catheter has a large diameter, the Seldinger method further comprises a step of incision of the skin with a scalpel at the puncturing point and of introduction of a dilator, prior to introduction of the catheter. The diameter of the dilator must be close to the external diameter of the catheter.

The flexible guide is generally formed by metallic coils and may comprise, according to the embodiments, a soft distal end bent over to form a J-shaped sleeve.

This method is currently being used for introducing catheters into veins. The dimension of the guide is selected as a function of the dimension of the catheter to be placed in the vein, to avoid injuring the patient. For this purpose, the external diameter of the guide is generally selected to be slightly smaller than the internal diameter of the catheter to be placed by this technique.

But to limit the risk of trauma to the patient, it is preferable that the puncturing needle, and therefore the guide, has a small diameter, which finally limits the dimension of catheters which may be placed and therefore the rate of the catheter. Also, because the guides are very small and the catheters very fragile, the latter may be damaged or altered by plication in the vein.

Therefore, the use of a set has been proposed comprising a rigid sheath threaded on a dilator tube, after withdrawal of the puncturing needle. More precisely, the sheath and the dilator tube are introduced above the flexible guide, while the latter is in place in the vein. The dilator tube is then withdrawn, the sheath staying in place, then the catheter is put in place in the vein by threading it on the sheath. The sheath and the flexible guide may then be withdrawn, by leaving the catheter in place.

There is the problem however of making insertion and extraction in the body of the sheath easy, which is larger in diameter than the flexible guide, by reducing the risk of trauma for the patient, especially on introduction of the sheath and the dilator tube.

Also, to limit the risk of gas embolism, the operator generally obstructs the distal end of the catheter with his fingers until it is introduced in the puncturing point. But the risk of sucking air into catheter when it is introduced is still possible.

SUMMARY OF THE INVENTION

An aim of the invention is therefore to propose a novel introduction system of a catheter in a vein of a patient which avoids the above drawbacks and which in particular simply, rapidly and effectively introduces a large-diameter catheter and reduces the risk of trauma for the patient and plicature of the catheter.

Another aim of the invention is to enable simple and effective purging of the catheter during its introduction in the puncturing point, to reduce the risk of gas embolism.

For this, the invention proposes an introduction system of a catheter in a vein, said catheter having at least one opening, a proximal end and a distal end, the introduction system comprising:

a mandrel configured to slide in the opening of the catheter, and a connector, said connector comprising:

a distal coupler configured to be mounted on a proximal end of the catheter, a first proximal coupler configured to slidably receive the mandrel to enable introduction and sliding of said mandrel in the opening of the catheter through the distal coupler, and a second proximal coupler configured to be connected to a fluid source, said second proximal coupler being in fluidic communication with the distal coupler.

Some preferred though non-limiting features of the introduction system described hereinabove are the following, taken individually or in combination:

the mandrel has a tapered distal end, the mandrel comprises a metal spring, the introduction system further comprises a guide, an external diameter of the guide being less than an internal diameter of a distal end of the mandrel, the introduction system further comprises a dilator, an external diameter of the dilator being substantially equal to an external diameter of the catheter to be introduced, the introduction system further comprises a base having: an outlet configured to be connected to the first proximal coupler of the connector, an inlet extending in the extension of the outlet and configured to slidably receive the mandrel to enable introduction of said mandrel in the first coupler of the connector, and a coupler in fluidic communication with the outlet and configured to be connected to a fluid source to enable injection of fluid in the connector by means of the outlet of the base and of the first proximal coupler of the connector, the introduction system further comprises a catheter having at least one opening, and/or the catheter has a threaded distal end.

According to a second aspect, the invention also proposes a connector for an introduction system as described hereinabove, said connector comprising a first proximal coupler, a second proximal coupler and a distal coupler, characterized in that:

the distal coupler of the connector is configured to be mounted on a proximal end of a catheter having at least one opening, the first proximal coupler of the connector is configured to receive a mandrel sliding to enable introduction and sliding of said mandrel in the opening of the catheter through the distal coupler, and the second proximal coupler of the connector is configured to be connected to a fluid source, said second proximal coupler being in fluidic communication with the distal coupler.

BRIEF DESCRIPTION OF THE DRAWINGS

Other features, aims and advantages of the present invention will emerge more clearly from the following detailed description and in conjunction with the appended drawings given by way of non-limiting examples and in which.

DETAILED DESCRIPTION OF AN EMBODIMENT

An introduction system 1 of a catheter 2 in a vein will now be described. Hereinbelow, the catheter 2 has at least one opening 3, for example between an opening 3 and five openings 3. The number of openings 3 of the catheter 2 however has no impact on the introduction system 1 of the invention, which enables introduction of any type of catheter 2 in a vein, irrespective of its diameter.

The introduction system 1 comprises:
a mandrel 10 configured to slide in the opening 3 of the catheter 2, and
a connector 20 comprising a first proximal inlet 22 (hereinbelow guide inlet 22), a second proximal inlet 24 (hereinbelow injection inlet 24) and a distal outlet 26.

"Proximal" will be designated as an element (such as an end, an inlet, a coupler, etc.) hereinbelow, extending to near an operator in use, as opposed to "distal" which will designate an element extending away from an operator in use.

The distal outlet 26 of the connector 20 is configured to be mounted on a proximal end 2a of the catheter 2. For this purpose, the catheter 2 may especially be inserted by force in or on the distal outlet 26, or as a variant be fixed by means of any other conventional means to the distal outlet 26.

The guide inlet 22 of the connector 20 as such is configured to slidably receive the mandrel 10 to enable its introduction and its sliding in one of the openings 3 of the catheter 2 through the distal outlet 26. The guide inlet 22 and the distal outlet 26 are in fluidic communication.

Finally, the injection inlet 24 is configured to be connected to a fluid source to enable injection of a fluid in the catheter 2. For this, the injection inlet 24 and the distal outlet 26 are in fluidic communication.

The introduction system 1 thereby introduces a mandrel 10 in the catheter 2 to make it easy to place the catheter 2 in a vein.

The introduction system 1 may further comprise or be used with a soft guide 4 to enable mounting and guiding of the mandrel 10 and of the catheter 2 in the vein. For example, the soft guide 4 may comprise a straight guide or a guide whereof a distal end is softer and incurved to form a J-shaped sleeve and make its introduction in the vein easier. The guide 4 may especially comprise metallic coils.

Since these types of flexible guides 4 are conventionally used in the Seldinger technique, they will not be detailed further here.

Finally, the introduction system 1 may comprise or be used with a dilator 5, i.e., a tube configured to widen a puncturing point and thus enable introduction of a catheter 2 whereof the diameter is greater than that of the soft guide 4.

The dilator 5 may be made of a plastic material of polyolefin type, for example polypropylene.

Since these types of dilators 5 are conventionally used in the Seldinger technique, they will not be detailed further here.

Optionally, the distal end 5b of the dilator 5 may be tapered to reduce the surface of the dilator 5 capable of abutting against the tissue of the patient during its introduction in the puncturing point.

The Mandrel 10

The mandrel 10 has a proximal end and a distal end 10b. It is evident that the mandrel 10 is inserted in the guide inlet 22 by its distal end 10b. The mandrel 10 is also hollow so it may be mounted on the guide 4 and guided into the vein.

To enable introduction of a catheter 2 in a vein so as not to cause trauma for a patient, irrespective of the diameter of the catheter 2, the distal end 10b of the mandrel 10 is tapered. For example, the external diameter of the mandrel 10 may be reduced progressively towards its distal end 10b over a distance (along the mandrel 10, between its proximal end and its distal end 10b) of between 0.3 cm and 2 cm.

For this purpose, a rigid end piece of tapered form may for example be applied to and fixed on the distal end of the mandrel 10.

In fact, it is the external diameter of the mandrel 10 which determines the diameter of the catheter 2 which may be introduced in the vein. So, when the distal end 10b of the mandrel 10 has no taper, the external diameter of the body of the mandrel 10 is the same as the external diameter of its distal end 10b. Also, the external diameter of the distal end 10b of the mandrel 10 is limited to the extent where, the greater it is the greater the risk of blood spill, and trauma for the patient and the impossibility (when the diameter is too large) of introducing the mandrel 10 in the vein. Consequently, tapering of the distal end 10b of the mandrel 10 both conserves a small external diameter for the distal end, ensuring easy introduction in the vein without trauma, and increases the diameter of the body of the mandrel 10 which may be used and therefore the diameter of the catheter 2 which may be introduced in the vein.

Optionally, the catheter 2 may also have a tapered distal end 2b for easy introduction in the vein.

The mandrel 10 is soft and flexible to limit the risk of damage to the catheter 2 during its introduction. For example, the mandrel 10 is hollow and may comprise a metal spring.

The coils of the spring define a central passage and are preferably joined at their free ends to prevent the latter from coming apart during use. If needed, the coils of the mandrel 10 may be welded or stuck at its distal end 10b to avoid uncoiling of the mandrel 10 when being withdrawn, for example when the path into the vein is very sinuous (especially the case for subclavian introduction), and remain disconnected between its proximal end and its distal end 10b to ensure the softness of the mandrel 10.

For example, in a first embodiment, the metal spring 10 may be made by withdrawing the core of a soft mandrel conventionally used in the Seldinger technique, thus forming the central passage. The resulting mandrel 10 is therefore hollow and has a softness adapted particularly so as not to traumatize the patient and be guided easily by the operator when placed in the vein.

By way of variant, the metal spring 10 may be made directly without a core and comprise a series of coils, which are preferably joined (i.e., attached) at its proximal end and its distal end 10b and not joined between its two ends.

The Connector 20

The guide inlet 22, the injection inlet 24 and the distal outlet 26 together form a Y-shaped connector 20.

The guide inlet 22, the injection inlet 24 and the distal outlet 26 extend substantially in a same plane P1. Also, the guide inlet 22 and the injection inlet 24 extend substantially symmetrically relative to a plane P2 perpendicular to the plane P1 and passing through the distal outlet 26. It is understood that this symmetrical configuration of the guide inlet 22 and of the injection inlet 24 is not limiting, the angle between the guide inlet 22 and the plane which may be greater or smaller than the angle between the injection inlet 24 and the plane, without however modifying the invention.

An angle between the plane and the guide inlet 22 is preferably less than 60° so as not to damage the mandrel 10 during its introduction into and its withdrawal from the opening 3 of the catheter 2.

For easy introduction of the mandrel 10 in the connector 20 and in the catheter 2, the introduction system 1 may further comprise a base 30 connected to the guide inlet 22, for example by means of a tube 44. Here, the base 30 is a T shape. By way of variant, the base may be a Y shape.

The base 30 comprises:

an outlet coupler 32 configured to be attached to the guide inlet 22 of the connector 20, a first proximal coupler 34 extending in the extension of the outlet coupler 32 and configured to receive the mandrel 10 so it may be introduced in the guide inlet 22 of the connector 20, and a second proximal coupler 36 in fluidic communication with the outlet coupler 32 and configured to be connected to a fluid source 38 to enable injection of fluid in the connector 20 and accordingly purge the catheter 2 prior to its introduction in the vein.

In a first embodiment, the outlet coupler 32 of the base 30 is connected to the guide inlet 22 of the connector 20 by means of a tube. The tube may be applied to and fixed on the connector 20 and on the base 30 by conventional means, typically by adhesion, over-injection or forced insertion.

Figure 5:
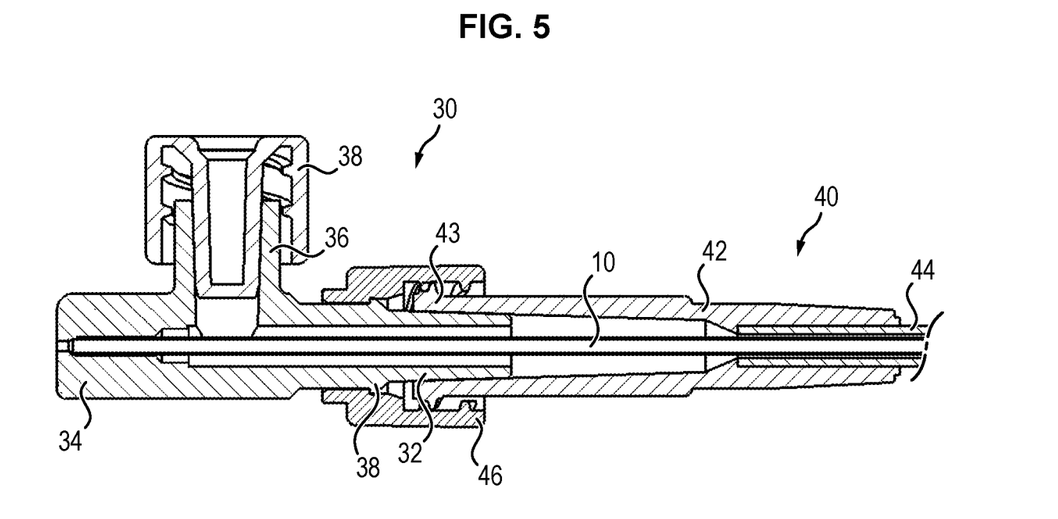
FIG. 5 is a sectional view of an embodiment of a T-shaped base of an introduction system according to the invention.
Figure 6:
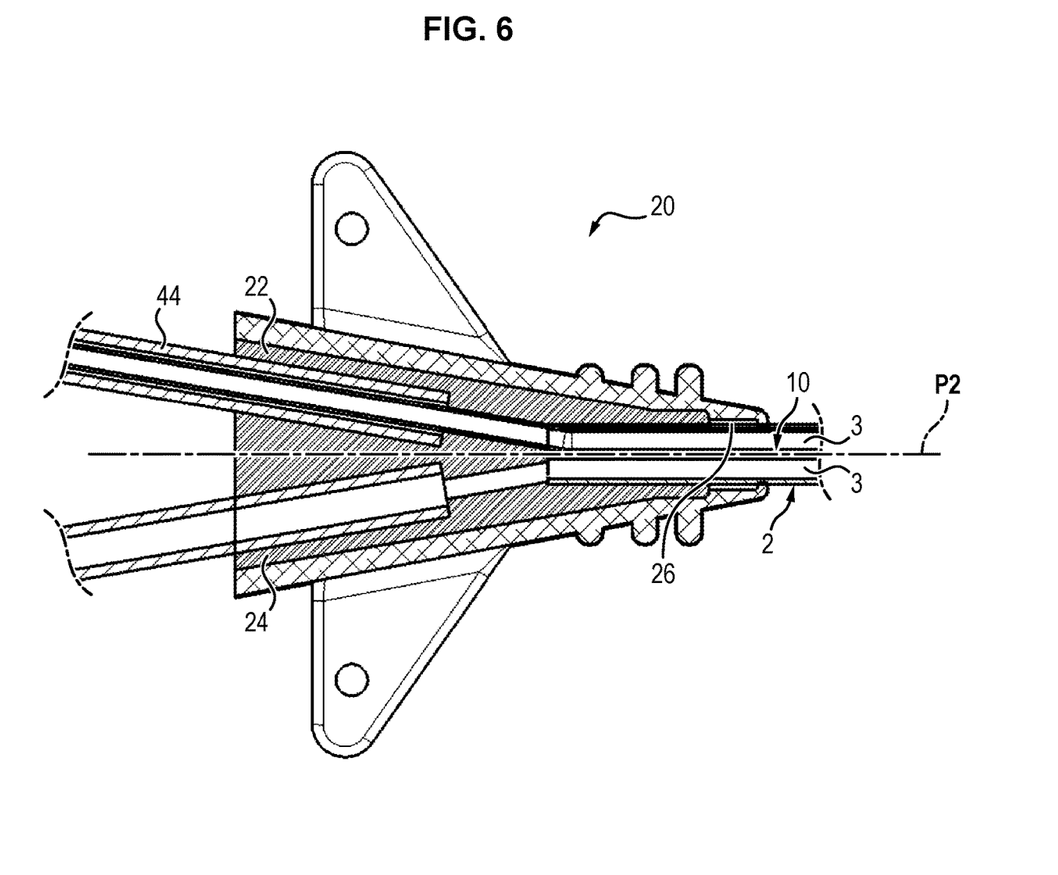
FIG. 6 is a sectional view of an embodiment of a connector of an introduction system according to the invention.
Figure 7:
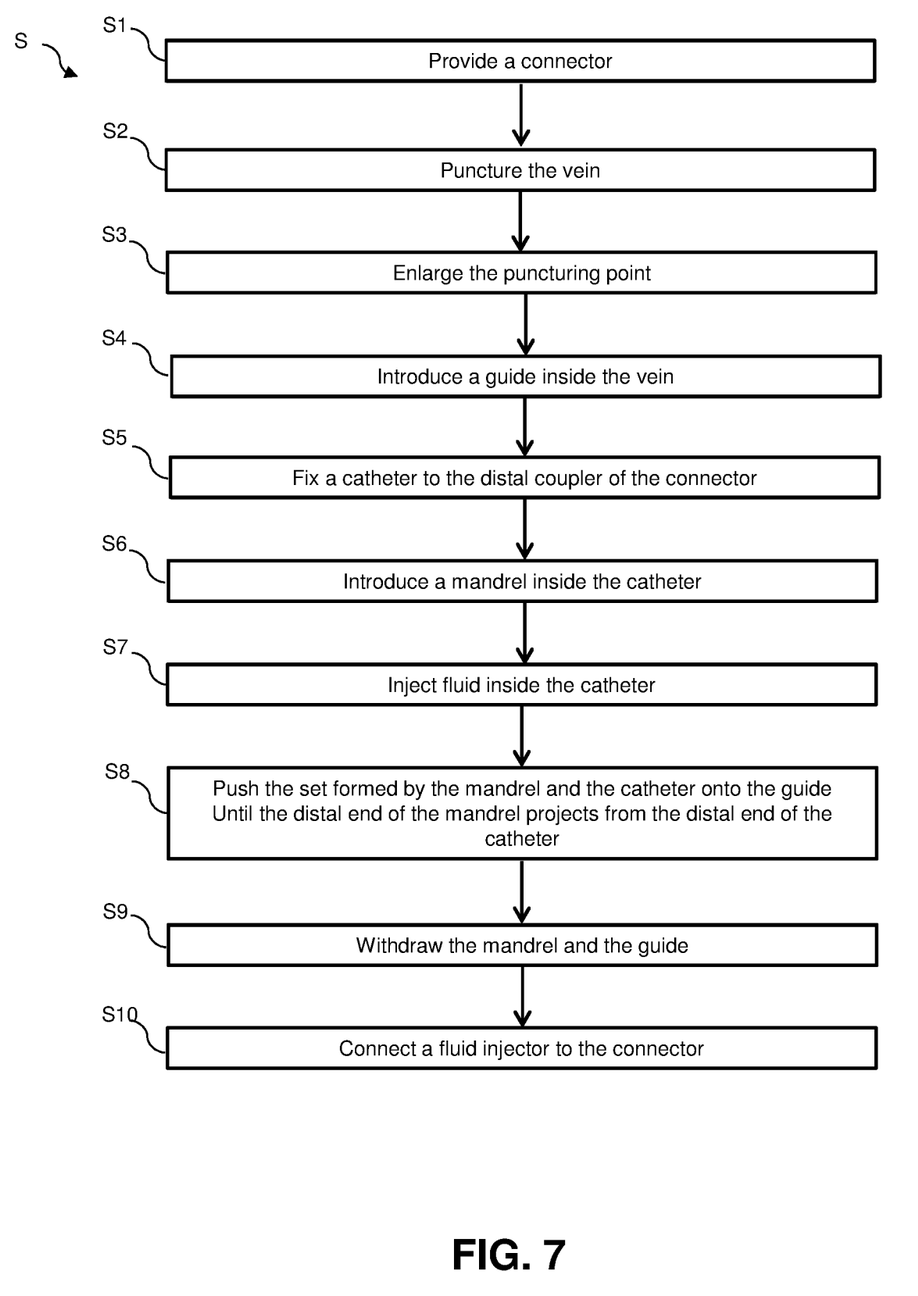
FIG. 7 is an organigram representing different steps of a method for introducing a catheter in a vein according to the invention.

In a second embodiment illustrated in FIG. 5, the outlet coupler 32 is connected to the guide inlet 22 by means of an introducer 40 comprising, as is known per se, a housing 42 and a tube 44. The housing 42 has a generally tubular form and has a distal end fixed on the tube 44 and a proximal end fitted with a connecting member 43. The introducer 40 (housing 42+tube 44) is hollow to enable passage of a guide 4, a mandrel 10 and a fluid. Finally, the outlet coupler 32 is itself equipped with a connecting member 33 for fastening the base 30 on the housing 42 of the introducer 40. For example, the connecting members 43, 33 of the housing 42 and of the outlet coupler 32 may be of Luer or Luer Lock type, or as a variant be connected by means of an intermediate connector 46, in which case the connecting members 33, 43 and the intermediate connector 46 may comply with the system described in document FR 2 996 141 in the name of the applicant.

In this second embodiment, the tube 44 may be applied to and fixed on the housing 44 and on the guide inlet 22 by conventional means, typically by adhesion or by over-injection.

The first proximal coupler 34 of the base 30 has an overall tubular form and is configured to enable introduction of the mandrel 10 and of the guide 4 in the base 30 to let them slide, if needed via the introducer 40, through the connector 20 and the catheter 2. The first proximal coupler 34 further comprises a proximal hole configured to enable introduction and passage of the guide 4 in the introduction system 1. For this purpose, the diameter of the proximal hole is slightly greater than the external diameter of the guide 4.

In an embodiment, the mandrel 10 is fixed in the opening of the first proximal coupler 34 of the base 30, for example by adhesion or by insertion by force. In this way, when the mandrel 10 is housed in the first proximal coupler, it prevents passage of a fluid coming from the second main coupler 36.

In a second embodiment, a septum may be housed sealed in the first proximal coupler 34. In this case, a passage is however formed in the septum to enable sealed introduction of the mandrel 10 in said coupler 34.

The second proximal coupler 36 of the base 30 extends in a direction substantially transversal to the direction of extension of the first proximal coupler 34 and of the outlet coupler 32. This second coupler 36 is configured to enable connection of a fluid injection device 38 for injecting a fluid of physiological serum type in the catheter 2 for the purpose of purging air and accordingly comprises a connecting member. For example, the fluid injection device 38 may comprise a syringe without needle fitted at the distal end of a connecting member complementary to that of the second proximal coupler 36. For example, the connecting members may comprise a connector of Luer or Luer Lock type (see for example FIG. 5).

The guide inlet 22 of the connector 20 and the distal outlet 26 therefore enable introduction and sliding of the mandrel 10 in the distal outlet 26 on the one hand and on the other hand injection of a fluid, typically physiological serum, in the distal outlet 26 then in the catheter 2 to purge the catheter 2 before it is placed in the vein.

To enable this purging, the outlet coupler 32 and if needed the introducer 40 are preferably dimensioned so as to authorize sliding of the mandrel 10 and of the guide 4 while enabling passage of a fluid around the mandrel 10. In this way, the internal diameter of the outlet coupler 32 and of the introducer 40 is larger than the external diameter of the mandrel 10 so as to form a passage for fluid injected by the second coupler 36 around the mandrel 10. During purging, it is evident that the mandrel 10 and if needed the septum housed in the first proximal coupler 34 prevent passage and outlet of fluid via said first coupler 34.

As indicated earlier, the injection inlet 24 is configured to be connected to a fluid source 6. Any standard connection means between the injection inlet 24 and the fluid source may be used. Typically, the fluid source which may be connected to the injection inlet 24 may comprise a syringe without needle or a pocket of fluid (not illustrated in the figures). The fluid source and the inlet may be connected directly to the injection inlet 24 or as a variant by means of a tube 25. The tube 25 may be applied to and fixed on the injection inlet 24 of the connector 20 and on the fluid source by conventional means, typically by adhesion, by over-injection or by insertion by force.

Method S for Introducing a Catheter 2

An embodiment of a method S for introducing a catheter 2 by means of the introduction system 1 as described hereinabove will now be described. This description will be given in relation to an introduction system 1 adapted for introducing a catheter 2 having two openings 3 whereof the external diameter is 27G (or around 9 mm) on a guide 4 of small diameter to limit the risk of trauma for patients. For such a catheter 2, an introduction system 1 may be selected for example comprising a mandrel 10 comprising a metal spring having an external diameter of the order of 1.10 mm to 1.30 mm. Here, the mandrel 10 and the catheter 2 have a tapered distal end. The dilator 5 has an external diameter equal to the external diameter of the catheter 2 (at the body of the catheter 2). Finally, the introduction system 1 comprises a base 30 including an introducer for easier introduction of the mandrel 10 in the catheter 2 and to enable purge of the set prior to and during placing.

This is not however limiting, as other dimensions of mandrel 10 and of dilator 5 may be implemented, the latter being simply dictated by the dimensions of the catheter 2 to be introduced in the vein. Also, the mandrel 10 may be made of other materials and comprise for example a soft sheath and not metallic coils. Finally, the base 30 and the introducer are optional.

During a first step S2 of the method, a vein in which a catheter 2 is to be introduced is punctured conventionally by means of a puncturing needle 6 of trocar type. Optionally, the puncturing needle 6 may be guided by echography or any other contrast radiographic exploration technique.

To reduce the risk of trauma for the patient, the puncturing needle 6 and the guide 4 are preferably selected so as to have a small internal diameter and a small external diameter, respectively.

For example, the guide 4 may have an external diameter of 0.46 mm. The internal diameter of the puncturing needle 6 may therefore be 0.55 mm for an external diameter of 0.80 mm. Such a needle 6 in fact simply, rapidly and atraumatically places a guide 4 of diameter of 0.46 mm.

This is not however limiting, as other dimensions of guide 4 and needle 6 may be used.

Figures 1A, 1C:
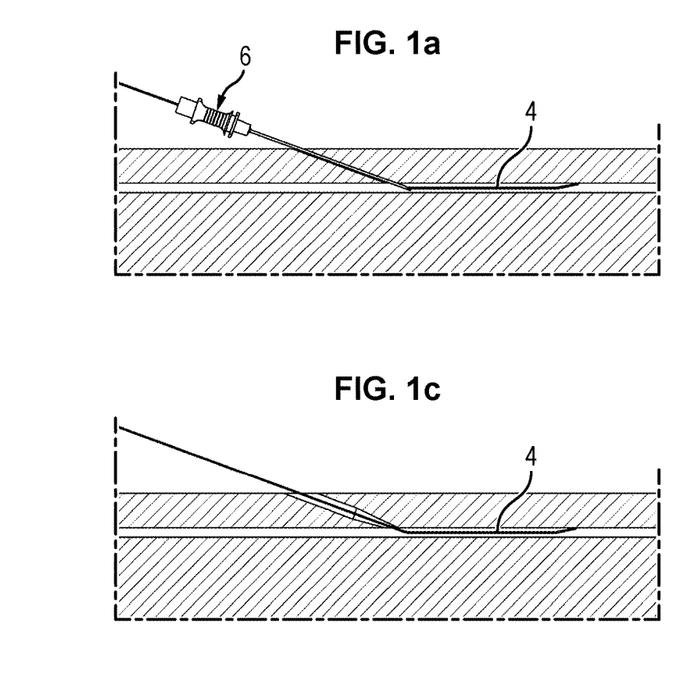
FIGS. 1(a) to 1(e) illustrate steps of a method for introducing a catheter in a vein of a patient by means of an example of an introduction system according to the invention.

During a second step S4, the guide 4 may then be inserted in the opening 3 of the puncturing needle 6 and introduced in the vein (see FIG. 1(a)). The puncturing needle 6 may then be withdrawn by sliding along the guide 4, the guide 4 staying in place in the vein.

The guide 4 may especially be provided with marking, for example radio-opaque marking, for viewing its position in the vein. Since introduction of a soft guide 4 by means of a needle is known per se, it will not be described further here.

Figures 1B, 1D:
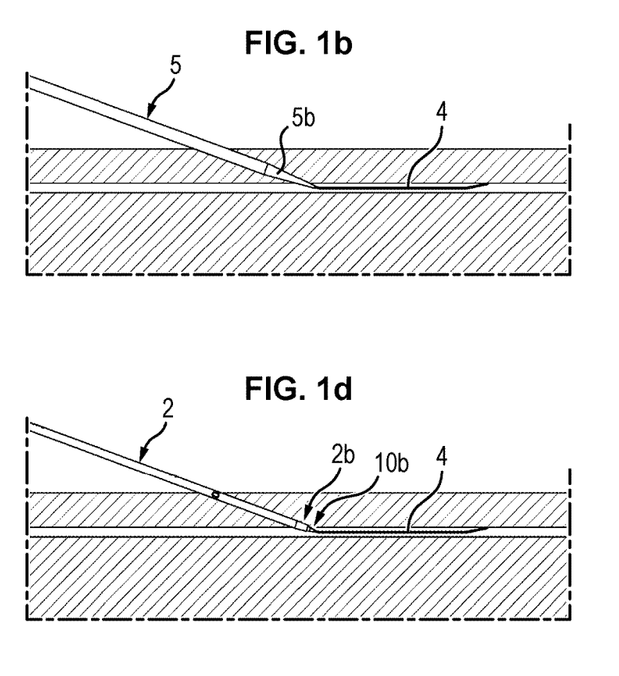

During a third step, the dilator 5 may be mounted on the guide 4 to widen the puncturing point (FIG. 1(b)).

For this, the proximal end of the guide 4 is introduced in the distal end of the dilator 5 and then the dilator 5 is slid along the guide 4 to the level of the puncturing point. If needed, the dilator 5 may be inserted in rotation in the puncturing point to facilitate its penetration. If needed, the tapered distal end 5b of the dilator 5 reduces the radial abutment formed by the dilator 5 as it enters the puncturing point, and therefore limits trauma for the patient.

Optionally, the puncturing point may also be enlarged (step S3) by making a surgical incision, especially if the aim is to introduce a catheter 2 of large diameter.

The dilator 5 may then be withdrawn (FIG. 1(c)).

During a fourth step, the catheter 2 may be mounted on the guide 4 and be introduced in the vein (FIG. 1(d)).

For this purpose, during a first sub-step, the catheter 2 is first fixed on the outlet of a connector 20 (step S5). Then the mandrel 10 is introduced in the catheter 2 (step S6), by having it pass successively via the first proximal coupler 34 and the outlet coupler 32 of the base 30, the introducer 40, the guide inlet 22 and finally the outlet of the connector 20. The mandrel 10 is pushed into the catheter 2 until its distal end 10b projects from the distal end 2b of the catheter 2. The entire tapered part 10b of the distal end of the mandrel 10 preferably exits the catheter 2 to decrease the radial surface capable of abutting against the puncturing point (see FIG. 4) and enabling progressive introduction of the set in the vein.

Figure 4:
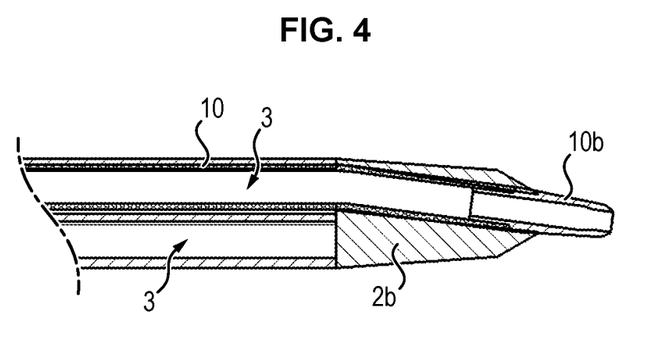
FIG. 4 is a sectional view of an example of a multi-opening catheter which may be used with an introduction system according to the invention, from which a mandrel of an introduction system projects.

In the event where the distal end 2b of the catheter 2 is also tapered, the abutment surface is all the more reduced. The risk of blood loss is therefore considerably lowered in comparison to the use of a conventional introduction system, by way of the very small puncturing point required and tapering of the mandrel 10 and if needed of the catheter 2.

The mandrel 10 is kept in this position by an operator.

During a second sub-step S7, optional, fluid (typically physiological serum) may be injected in the catheter 2 and the hollow mandrel 10 to purge the air they contain and avoid any risk of gas embolism. For this, a syringe 38 (or any equivalent injection device) containing the selected fluid is connected to the second proximal coupler 36 of the base 30 then at least partially emptied in the catheter 2 by means of the connector 20 until air contained in the catheter 2 and in the mandrel 10 is purged.

Next, during a third sub-step S8, the catheter 2 (in which the mandrel 10 is housed) is introduced in the vein by having it slide on the guide 4 until its distal end 2b reaches the intended zone of the vein. It is evident that this gesture is identical to that normally used by an operator as per the Seldinger method, since it suffices to have the catheter 2 slide on the guide 4. There is therefore no risk of error resulting from misunderstanding of the handling to be carried out by the operator, once the introduction system 1 is assembled.

If needed, fluid may be further injected in the catheter 2 and in the mandrel 10 via the syringe 38 connected to the second coupler 36 when introduced to the vein to ensure that no air bubble forms in the vein.

It is evident that the presence of the mandrel 10 in the catheter 2 further reduces the radial surface abutting with the puncturing point, stiffens the catheter 2 despite its large diameter and easily follows the guide 4 (despite the large size of the catheter 2), preventing any risk of plicature of the catheter 2 and injury to the vein.

Figure 1E:
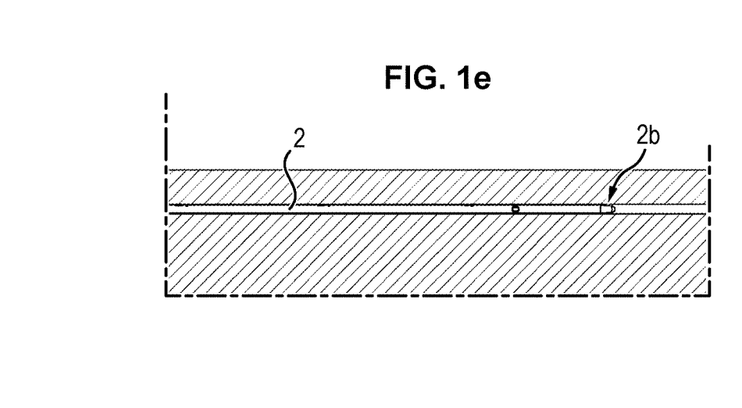
Figure 2:
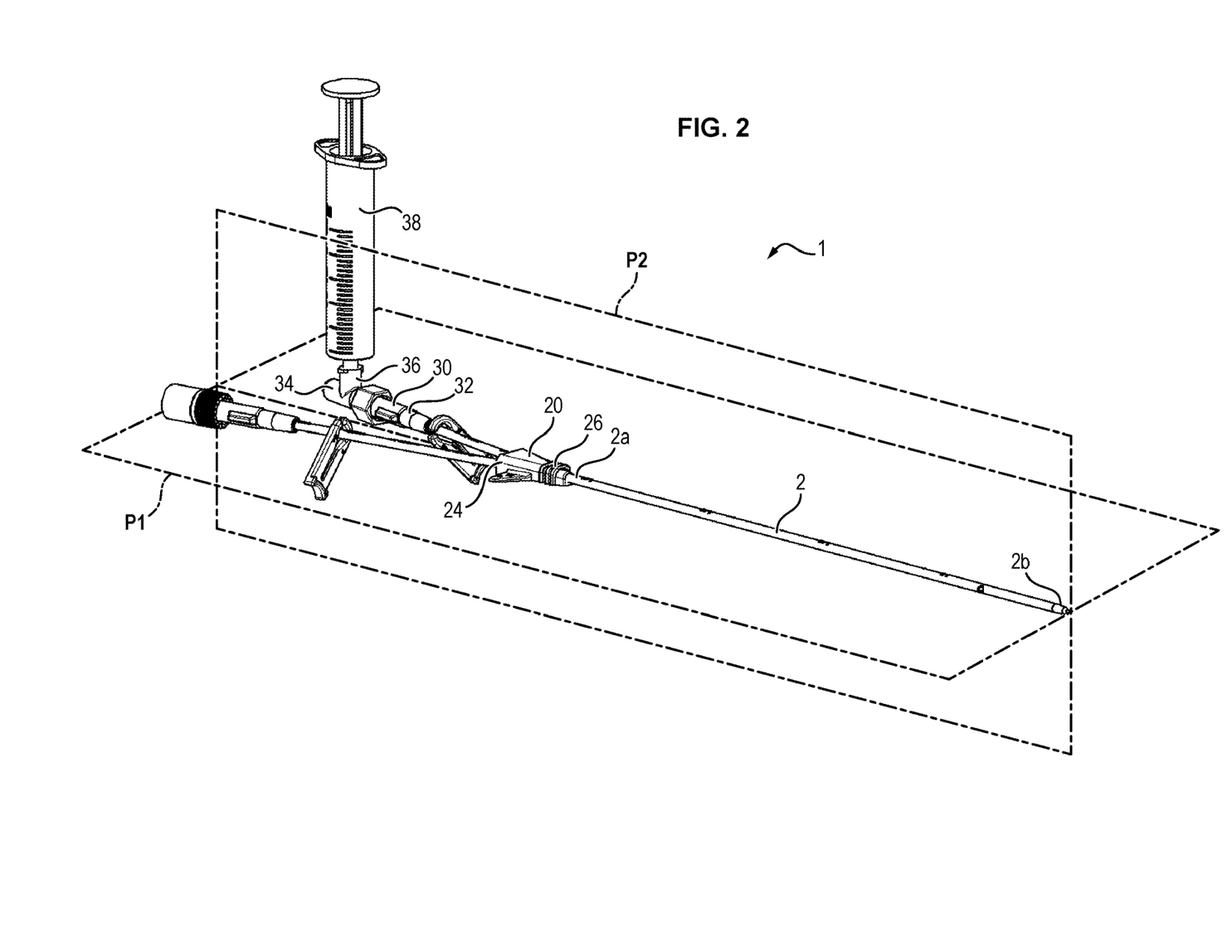
FIG. 2 is a perspective view of an embodiment of an introduction system according to the invention.

In a variant embodiment, the introduction system 1 may be provided pre-mounted, in which case the catheter 2 may be prefixed on the connector 20 and the mandrel 10 pre-inserted in its opening 3. The sub-steps for fastening the catheter 2 and introduction of the mandrel 10 are superfluous. During a fifth step S9, the mandrel 10 and the guide 4 may be withdrawn from the vein while leaving the catheter 2 in place (FIG. 1(e)).

Figure 3:
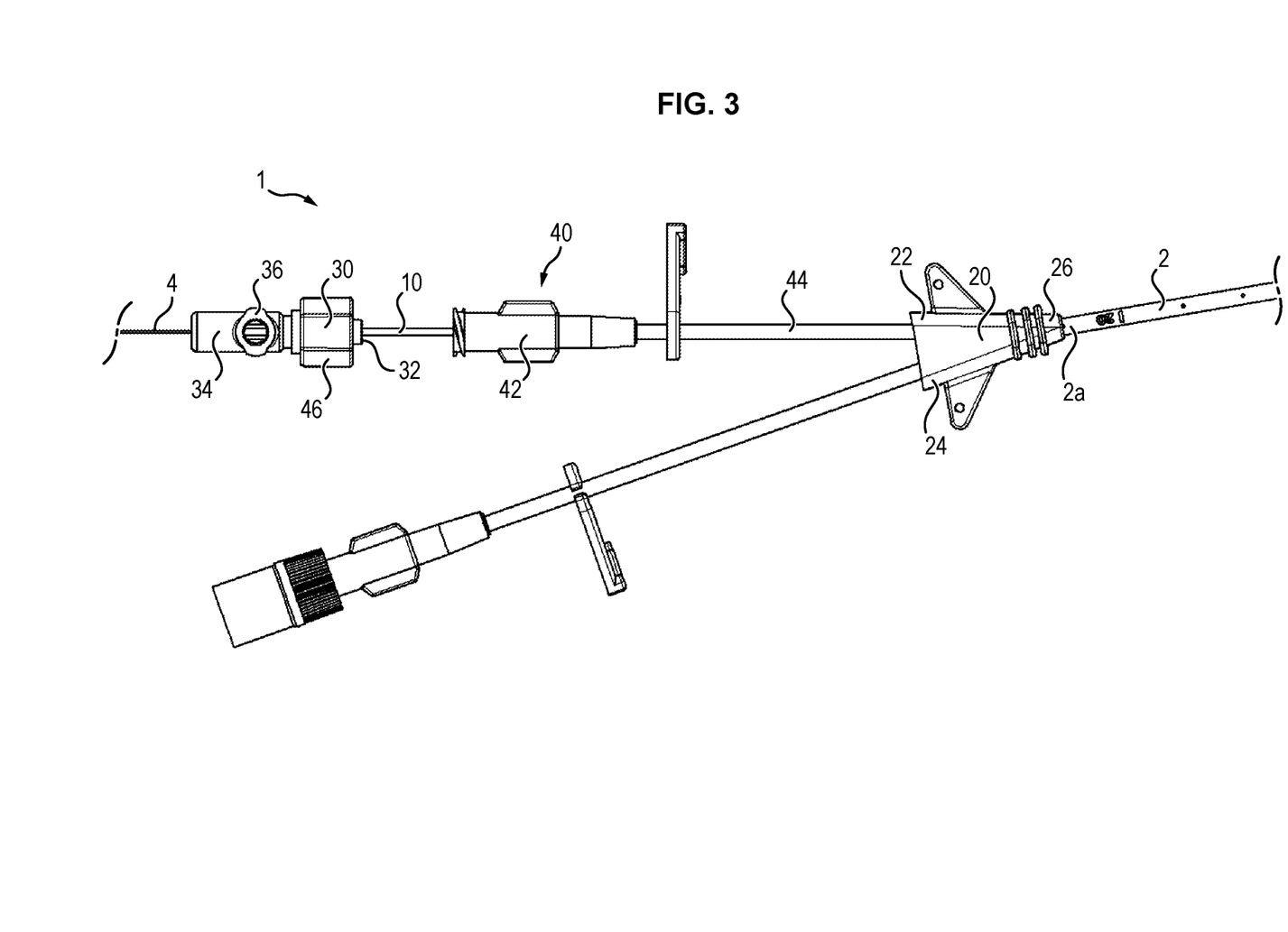
FIG. 3 is a plane view of the introduction system of FIG. 2, during withdrawal of the mandrel.

In an embodiment, the mandrel 10 and the guide 4 are withdrawn simultaneously (FIG. 3). In this case, the gesture of the operator is not modified in comparison with the conventional Seldinger method, which is reassuring for the operator and avoids the risk of error. By way of variant, the mandrel 10 and the guide 4 may be withdrawn successively.

If needed, a fluid may then be injected via the injection inlet 24 in the catheter 2, and then into the vein. For this, a fluid injection device such as a syringe or a fluid pocket is connected to the injection inlet 24 of the connector 20 (step S10).

The invention claimed is:

1. A method for introducing a catheter in a vein comprising the following steps:
   puncturing the vein so as to form a puncturing point;
   introducing a guide in the punctured vein;
   introducing a mandrel into a connector and through a first coupler of a base, the base operatively coupled to the connector at the first coupler of the base, the connector having a catheter fixed thereto, the connector comprising a distal outlet, a first proximal inlet, and a second proximal inlet, wherein the catheter is fixed to the connector at the distal outlet of the connector, wherein each of the first proximal inlet and the second proximal inlet is in fluid communication with the distal outlet, wherein neither the first proximal inlet nor the second proximal inlet is coaxial with the distal outlet, wherein the mandrel is introduced through the first proximal inlet, through the distal outlet, of the connector and into the catheter until a distal end of the mandrel projects from a distal end of the catheter;
   introducing the catheter having the mandrel therein in the punctured vein by sliding the catheter having the mandrel therein onto the guide;
   withdrawing the mandrel and the guide; and
   connecting a fluid injection device to the second proximal inlet of the connector.

2. The introduction method according to claim 1, wherein the puncturing step is conducted using a puncturing needle.

3. The introduction method according to claim 1, wherein the introduction step of the guide is conducted using a puncturing needle.

4. The method according to claim 1, further comprising, prior to introducing the catheter having the mandrel therein in the punctured vein, widening the puncturing point.

5. The method according to claim 4, wherein widening the puncturing point comprises widening the puncture point using a dilator or by surgical incision.

6. The method according to claim 1, wherein the mandrel is fixed relative to the catheter while introducing the catheter having the mandrel therein in the punctured vein.

7. The method according to claim 1, wherein the guide and the mandrel are withdrawn simultaneously.

8. The method according to claim 1, wherein the guide and the mandrel are withdrawn successively.

9. The method according to claim 1, further comprising, after introducing the guide into the punctured vein and before introducing the catheter having the mandrel therein into the punctured vein, injecting a fluid in the catheter so as to purge any air contained therein.

10. The method according to claim 9, further comprising injecting a fluid in the catheter while introducing the catheter having the mandrel therein in the punctured vein.

11. The method according to claim 9, wherein the base further comprises a second coupler for coupling the base to a source of the fluid.

12. The method according to claim 1, wherein
   connecting the fluid injection device to the connector is conducted prior to withdrawing the guide and the mandrel.

13. The method according to claim 1, wherein each of the distal end of the catheter and the distal end of the mandrel is tapered, and wherein introducing the mandrel into the catheter until the distal end of the mandrel projects from the distal end of the catheter comprises introducing the mandrel into the catheter until the tapered distal end of the mandrel projects beyond the tapered distal end of the catheter so as to reduce a radial surface capable of abutting against the puncturing point.

14. The method according to claim 1, wherein the first proximal inlet is formed at a first angle relative to a central axis of the distal outlet of the connector and the second proximal inlet is formed at a second angle relative to the central axis of the distal outlet of the connector, wherein the first and second angles are acute.

15. The method of claim 14, wherein the first proximal inlet is formed at a third angle relative to the second proximal inlet, wherein the third angle is acute.

16. The method of claim 1, wherein operatively coupling the base to the connector comprises coupling an introducer to the base and to the connector such that the introducer extends between the base and the connector.

17. A method for introducing a catheter in a vein comprising:
   puncturing the vein so as to form a puncturing point;
   introducing a guide in the punctured vein;
   operatively coupling a base to a connector at a first coupler of the base;
   operatively coupling an introducer to the base and to the connector such that the introducer extends between the base and the connector;
   introducing a mandrel into the connector and through the first coupler of the base, the connector having a catheter fixed thereto, the connector comprising a distal outlet, a first proximal inlet, and a second proximal inlet, wherein the catheter is fixed to the connector at the distal outlet of the connector, wherein each of the first proximal inlet and the second proximal inlet is in fluid communication with the distal outlet, wherein neither the first proximal inlet nor the second proximal inlet is coaxial with the distal outlet, wherein the mandrel is introduced through the first proximal inlet, through the distal outlet, and into the catheter until a distal end of the mandrel projects from a distal end of the catheter;
   introducing the catheter having the mandrel therein in the punctured vein by sliding the catheter having the mandrel therein onto the guide;
   withdrawing the mandrel and the guide; and
   connecting a fluid injection device to the second proximal inlet of the connector.

18. A method for introducing a catheter in a vein comprising:
   puncturing the vein so as to form a puncturing point;
   introducing a guide in the punctured vein;
   introducing a mandrel into a connector having a catheter fixed thereto, the connector comprising a distal outlet, a first proximal inlet, and a second proximal inlet, wherein the catheter is fixed to the connector at the distal outlet of the connector, wherein each of the first proximal inlet and the second proximal inlet is in fluid communication with the distal outlet, wherein neither the first proximal inlet nor the second proximal inlet is coaxial with the distal outlet, wherein the mandrel is introduced through the first proximal inlet, through the distal outlet, and into the catheter until a distal end of the mandrel projects from a distal end of the catheter;
   after introducing the guide into the punctured vein, injecting a fluid in the catheter so as to purge any air contained therein before the catheter is introduced into the punctured vein;

introducing the catheter having the mandrel therein in the punctured vein by sliding the catheter having the mandrel therein onto the guide while injecting the fluid in the catheter;

withdrawing the mandrel and the guide; and connecting a fluid injection device to the second proximal inlet of the connector.

* * * * *